United States Patent [19]

Pfister et al.

[11] Patent Number: 4,889,866
[45] Date of Patent: Dec. 26, 1989

[54] ARYLSULFONYL DIHYDROPYRIDINE DERIVATIVES

[75] Inventors: Jurg R. Pfister, Los Altos; Roman Davis, Campbell; Chi-Ho Lee, Palo Alto, all of Calif.

[73] Assignee: Syntex (U.S.A.) Inc., Palo Alto, Calif.

[21] Appl. No.: 61,752

[22] Filed: Jun. 11, 1987

[51] Int. Cl.$^4$ .................... C07D 211/96; A61K 31/44
[52] U.S. Cl. .................... 514/347; 546/294
[58] Field of Search .................... 546/294; 514/347

[56] References Cited

U.S. PATENT DOCUMENTS

| | | | |
|---|---|---|---|
| 4,017,629 | 4/1977 | Habicht et al. | 546/321 |
| 4,370,334 | 1/1983 | Sato | 546/321 |
| 4,510,310 | 4/1985 | Wehinger et al. | 546/321 |
| 4,680,305 | 7/1987 | Wehinger et al. | 514/347 |

FOREIGN PATENT DOCUMENTS 2616995 10/1977 Fed. Rep. of Germany .

*Primary Examiner*—Jane T. Fan
*Attorney, Agent, or Firm*—Carol J. Roth; Derek P. Freyberg; Tom M. Moran

[57] ABSTRACT

Novel arylsulfonyl-dihydropyridine derivatives which are useful as calcium entry-blocker cardiovascular agents have the formula:

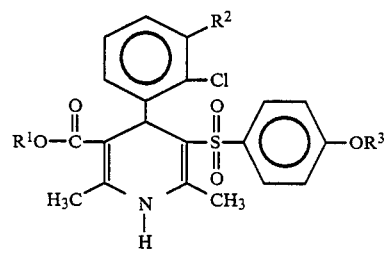

or a pharmaceutically acceptable salt thereof, wherein
$R^1$ is hydrogen, lower alkyl, or lower alkoxyalkyl;
$R^2$ is hydrogen or chloro; and
$R^3$ is hydrogen, lower alkyl, or lower alkoxyethyl.

A novel process using chiral sulfoxide reagents efficiently produces single isomers of these and other sulfonyl dihydropyridines.

10 Claims, No Drawings

ARYLSULFONYL DIHYDROPYRIDINE DERIVATIVES

BACKGROUND OF THE INVENTION

Field of the Invention

This invention relates to 4-phenyl-3-sulfonyl-1,4-dihydropyridine derivatives and the pharmaceutically acceptable salts thereof which are useful in the treatment of cardiovascular diseases such as hypertension, congestive heart failure, angina, migraine, and vasospastic disorders. The invention also relates to a pharmaceutically acceptable composition containing an effective amount of at least one of the compounds in combination with a suitable excipient, the composition being useful for the treatment of cardiovascular diseases such as hypertension, congestive heart failure, angina, or vasospastic disorders in mammals. The invention also relates to a process for making the compounds of the invention, and the use of compounds of the invention in pharmaceutical compositions useful for the treatment of cardiovascular diseases such as hypertension, congestive heart failure, angina, migraine, and vasospastic disorders in mammals.

The invention also relates to intermediates and processes for preparing single optically active isomers of the compounds of the invention and other sulfonyl dihydropyridines.

Related Disclosures

Certain 4-phenyl-3-sulfonyl-1,4-dihydropyridine derivatives are known. See, for example, U.S. Pat. No. 4,017,629, German Offenlegungsschrift No. 2,616,995, and German Offenlegungsschrift No. 3,501,695. These and other documents referred to in the specification of this application are hereby incorporated herein by reference.

SUMMARY OF THE INVENTION

The first aspect of this invention is the group of compounds represented by the Formula I

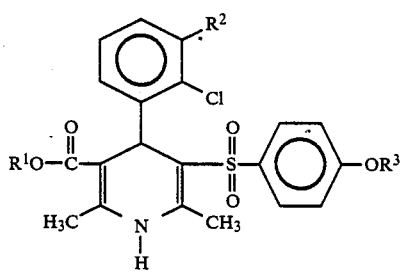

or a pharmaceutically acceptable salt thereof, wherein
$R^1$ is hydrogen, lower alkyl, or lower alkoxyalkyl;
$R^2$ is hydrogen or chloro; and
$R^3$ is hydrogen, lower alkyl, or lower alkoxyethyl.
These compounds are potent orally active antihypertensive agents of the calcium entry-blocker type.

Another aspect of the invention is a composition useful in the treatment of a cardiovascular disease in a mammalian subject treatable with a calcium entry-blocker, which composition comprises an effective amount of a compound of Formula I and a pharmaceutically suitable excipient.

Still another aspect of the invention is a method for treating cardiovascular diseases in mammalian subjects (especially man) treatable with a calcium entry-blocker, such as hypertension, congestive heart failure, angina, migraine, and vasospastic disorders which comprises administering an effective amount of at least one compound chosen from those represented by Formula I above, alone or as a part of a composition described above.

Still another aspect of the invention is a process for preparing single optically active isomers of the compounds represented by the following Formula I*:

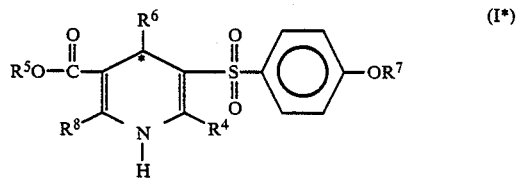

wherein
$R^4$ and $R^8$ are hydrogen, lower alkyl, $-NR^9R^{10}$, or nitro;
$R^5$ is hydrogen, lower alkyl, lower alkoxyalkyl, or phenyl optionally substituted by one or more substituents selected from the group consisting of lower alkyl, lower alkoxy, hydroxy, halogen, lower alkoxyalkyl, nitro, and $-NR^9R^{10}$;
$R^6$ is phenyl optionally substituted by one or more substituents selected from the group consisting of lower alkyl, lower alkoxy, hydroxy, halogen, nitro, azido, trifluoromethyl, trifluoromethoxy, difluoromethoxy, $-NR^9R^{10}$, lower alkoxyalkyl, cyano, lower acyl, or lower acyloxy; or
$R^6$ is

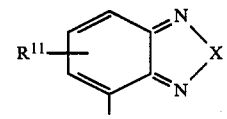

wherein X is oxygen or sulfur and $R^{11}$ is hydrogen, halogen, trifluoromethyl, nitro, hydroxy, lower alkyl, lower alkoxy, or lower alkoxyalkyl;
$R^7$ is hydrogen, lower alkyl, or lower alkoxyalkyl; and $R^9$ and $R^{10}$ are hydrogen or lower alkyl.

DETAILED DESCRIPTION OF THE INVENTION

Definitions

As used in the specification and appended claims, unless specified to the contrary, the following terms have the meaning indicated:

The term "lower alkyl" refers to a straight or branched chain monovalent radical consisting solely of carbon and hydrogen, containing no unsaturation and having from one to four carbon atoms, i.e. methyl, ethyl, n-propyl, i-propyl, n-butyl, i-butyl, s-butyl, and t-butyl.

The term "lower alkoxy" refers to a radical of the form $-OR_a$, where $R_a$ is lower alkyl as defined above. Examples of lower alkoxy groups are methoxy, ethoxy, n-propoxy, i-propoxy, butoxy, t-butoxy, and the like.

The term "lower alkoxyalkyl" refers to a radical of the form $-R_aOR_a$ where each $R_a$ is independently lower alkyl as defined above. Examples of lower alkoxyalkyl groups are methoxymethyl, ethoxyethyl, propoxymethyl, propoxybutyl, butoxypropyl, butoxybutyl, and the like.

The term "lower alkoxyethyl" refers to radicals of the form —CH$_2$—CH$_2$—O—R$_a$, where R$_a$ is lower alkyl as defined above. Examples of lower alkoxyethyl groups are methoxyethyl, ethoxyethyl, 2-(2-propoxy)ethyl, t-butoxyethyl, and the like.

The term "halogen" refers to chlorine, bromine, and iodine.

The term "lower acyl" refers to —C(O)R$_a$, where R$_a$ is lower alkyl as defined above.

The term "lower acyloxy" refers to —OC(O)R$_a$, where R$_a$ is lower alkyl as defined above.

The term "optionally" means that the subsequently described event or circumstances may or may not occur, and that the description includes instances where said event or circumstances occurs and instances in which it does not. For example, "phenyl optionally substituted" means that the phenyl may or may not be substituted and that the description includes both unsubstituted phenyl and phenyl wherein there is substitution.

The term "OXONE ®" refers to potassium peroxymonosulfate, which is an oxidizing reagent.

The term "TWEEN ® 80" refers to polyoxyethylene (20) sorbitan monooleate, which is a surfactant.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The nomenclature used herein is basically a modified form of I.U.P.A.C. nomenclature wherein compounds of the invention are named as derivatives of 1,4-dihydropyridine. The positions in the compounds are numbered beginning with the pyridine nitrogen and proceeding counter-clockwise in all drawings of the structure. For example, the following compound is named 2,6-dimethyl-5-methoxycarbonyl-4-(2-chlorophenyl)-3-(4-hydroxyphenyl)sulfonyl-1,4-dihydropyridine:

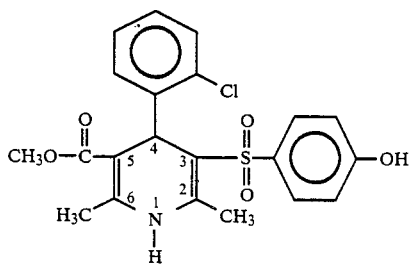

The compounds of the invention have a chiral center at the C-4 position of the dihydropyridine ring and exist as optical antipodes at that position. The invention described and claimed herein includes each of the individual C-4 isomers as well as their racemic and non-racemic mixtures. The isomers may be separated by various methods such as selective crystallization and column chromatography. See, for example, T. Shibanuma, et al., Chem. Pharm. Bull., 28, 2809–2812 (1980). Alternatively, the chiral compounds of the invention may be prepared using optically active reactants, or by a combination of separation and chiral synthesis. One aspect of the instant invention is a process for producing single isomers of optically active sulfonyl dihydropyridine compounds of Formul I* using a chiral sulfoxide as a starting material. Sulfoxide as a chiral center is known in the literature. See, for example, M. R. Barbachyn and C. R. Johnson, "Optical Activation and Utilization of Compounds Containing Chiral Sulfur Centers", Asymmetric Synthesis, (J. D. Morrison and J. W. Scott, Ed.), 1984, Vol. 4, pages 227–261.

The term "(±)" is used to designate a racemic mixture of individual (+) and (—) isomers. The (±) racemate as well as the individual (+) and (—) enantiomers and non-racemic mixtures thereof are included within the scope of this invention.

Preferred Embodiments

Within the several aspects of this invention which are set forth in the Summary of the Invention, certain subgroups are preferred. The metes and bounds of these subgroups and their relative degrees of preference are described below.

One aspect of the present invention is the group of compounds represented by the Formula (I)

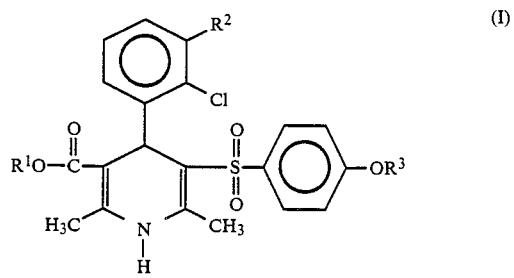

or a pharmaceutically acceptable salt thereof, wherein
R$^1$ is hydrogen, lower alkyl, or lower alkoxyalkyl;
R$^2$ is hydrogen or chloro; and
R$^3$ is hydrogen, lower alkyl, or lower alkoxyethyl.

Within this group of compounds, a preferred subgroup includes those compounds of Formula I in which R$^1$ is lower alkyl and R$^3$ is hydrogen or lower alkyl. Within this subgroup, a preferred class includes those compounds of Formula I in which R$^1$ is methyl and R$^3$ is hydrogen or methyl. Compounds especially preferred within this class are those in which R$^2$ is hydrogen. The (—) isomers of the compounds of the Formula I, and the preferred subgroups thereof, are preferred.

At the present time, the most preferred compounds of this invention are:

(—)-4-(2-chlorophenyl)-3-(4-hydroxyphenyl)sulfonyl-5-methoxycarbonyl-2,6-dimethyl-1,4-dihydropyridine; and (—)-4-(2-chlorophenyl)-3-(4-methoxyphenyl)sulfonyl-5-methoxycarbonyl-2,6-dimethyl-1,4-dihydropyridine.

Formulation and Administration

Another aspect of the present invention relates to a pharmaceutical composition useful in the treatment of cardiovascular diseases in mammalian subjects (especially man) treatable with a calcium entry-blocker, such as hypertension, congestive heart failure, angina, migraine, and vasospastic disorders, particularly in the treatment of hypertension or congestive heart disease in man, which composition comprises a therapeutically effective amount of a compound of Formula I, in admixture with a pharmaceutically acceptable excipient. A therapeutically effective amount is that amount which, when administered to a mammal in need thereof, is sufficient to effect treatment, as defined above. Thus, the level of the drug in the formulation can vary from about 5 percent weight (%w) to about 95%w of the drug based on the total formulation and about 5%w to 95%w excipient. Preferably the drug is present at a level of about 10%w to about 70%w.

Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

Another aspect of the present invention relates to a method for treating cardiovascular diseases in mammalian subjects (especially man) treatable with a calcium entry-blocker, such as hypertension, congestive heart failure, angina, migraine, and vasospastic disorders, particularly hypertension or congestive heart disease in man, which method comprises administering a therapeutically effective amount of a compound of Formula I, to a subject in need thereof.

In the practice of the above described method of the present invention a therapeutically effective amount of the compound of Formula I or a pharmaceutical composition containing same is administered via any of the usual and acceptable methods known in the art, either singly or in combination with another compound or compounds of the present invention or other pharmaceutical agents. These compounds or compositions can thus be administered orally, systemically (e.g. transdermally, intranasally or by suppository) or parenterally (e.g. intramuscularly, subcutaneously and intravenously), and can be administered either in the form of solid or liquid dosages including tablets, solutions, suspensions, aerosols, and the like, as discussed in more detail above. It is preferred to administer compounds of Formula I orally.

The formulation can be administered in a single unit dosage form for continuous treatment or in a single unit dosage form ad libitum when relief of symptoms is specifically required.

The Spontaneously Hypertensive Rat (SHR) assay is an accepted test for determining antihypertensive activity. See, e.g., J. Roba, et al., *Arch. Int. Pharmacodyn.*, 200, 182 (1972). Other widely accepted tests for determining calcium entry-blocking activity include rat aortic strip assays, anesthetized dog assays, and ultrasonic two-dimensional echocardiography. See, e.g., P. Gueret et al., *Circulation*, 62(6), 1308 (1980), and M. Tripp, *American J. of Physiology*, 232(2), H173 (1977). The compounds of the invention exhibit antihypertensive activity in the SHR assay and other assays.

In view of the foregoing as well as in consideration of the degree of severity of the condition being treated, age of subject and so forth, all of which factors are determinable by routine experimentation by one skilled in the art, the effective dosage in accordance herewith can vary over a wide range. Generally, a therapeutically effective amount ranges from about 1.0 to about 100 mg/kg body weight per day and preferably, for example, for antihypertensive use, from about 3 to about 50 mg/kg body weight per day. In alternative terms, for an average 70 kg adult human subject, a therapeutically effective amount in accordance herewith would be, in preferred embodiments from about 70 mg to about 7.0 g per day per subject, and preferably from about 210 mg to 3.5 g per day per subject. Generally, a therapeutically effective amount for the treatment of congestive heart disease ranges from about 1.0 to about 100 mg/kg body weight per day, and preferably from about 30 to about 50 mg/kg body weight per day. In alternative terms, for an average 70 kg adult human subject, a therapeutically effective amount in accordance herewith would be, in preferred embodiments from about 70 mg to about 7.0 g per day per subject, and preferably from about 210 mg to 3.5 g per day per subject.

PREPARATION OF THE INVENTION

Compounds of Formula C

The compounds of Formula I are synthesized from the compounds of Formula C which are prepared as shown in the following Reaction Scheme I:

REACTION SCHEME I

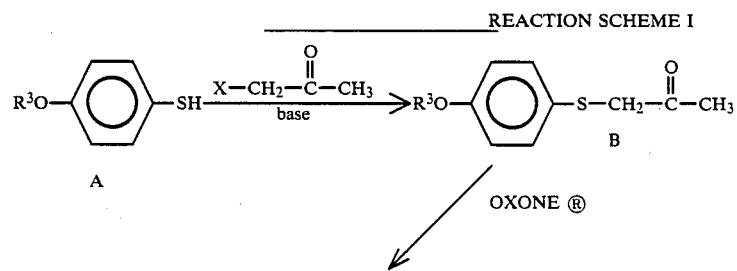

-continued
REACTION SCHEME I

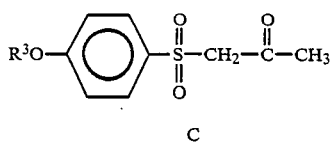

C wherein:
X is halogen; and
$R^3$ is hydrogen, lower alkyl, or lower alkoxyethyl.

Compounds of Formula A are commercially available from, inter alia, Aldrich Chemical Co. Alternatively, they can be prepared by standard methods known to those skilled in the chemical art.

The compounds of Formula C are prepared by first reacting compounds of Formula A with an α-haloacetone to form compounds of Formula B. Compounds of Formula A are reacted with about 1 molar equivalent of a strong base, e.g. an alkali metal hydroxide, preferably sodium hydroxide, in a protic solvent, e.g. a mixture of water and a lower alkanol, preferably methanol. The reaction is conducted at a temperature of about $-10°$ C. to 20° C., preferably about 0° C. An α-haloacetone, preferably chloroacetone, is then added and stirred about 1–30 minutes, typically about 5 minutes, to form compounds of Formula B.

Compounds of Formula B are then converted to compounds of Formula C utilizing a suitable oxidizing agent, for example OXONE ®, which is commercially available from Aldrich Chemical Co. The oxidizing agent, about 3 molar equivalents slurried in water, is added to the above solution of compound B. After about 1–30 minutes, typically about 5 minutes, the mixture is filtered and the compounds of Formula C are isolated from the filtrate by conventional means, e.g. precipitation from an aqueous solution of the sodium salt by addition of acid.

Compounds of Formula I

The preparation of compounds of Formula I is shown in the following Reaction Scheme II:

REACTION SCHEME II

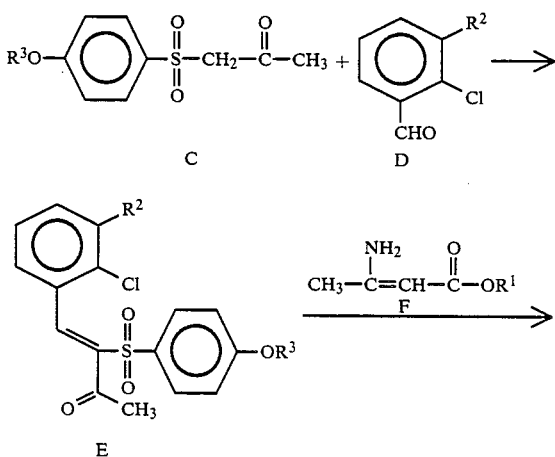

-continued
REACTION SCHEME II

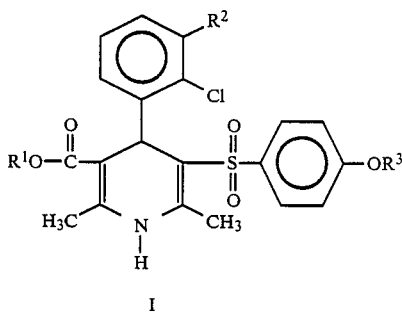

I wherein:
$R^1$ is hydrogen, lower alkyl, or lower alkoxyalkyl;
$R^2$ is hydrogen or chloro; and
$R^3$ is defined as in Reaction Scheme I.

Compounds of Formula D and Formula F are commerically available from, i.a., Aldrich Chemical Company. Compounds of Formula C are reacted with a 2-chlorobenzaldehyde derivative of Formula D under Knoevenagel condensation conditions (see, e.g., G. Jones, Organic Reactions 15, 204, 1967) to form a benzylidene derivative of Formula E, which is then reacted with a β-aminocrotonate (compounds of Formula F) to form a 4-phenyl-2,6-dialkyl-3-phenylsulfonyl-1,4-dihydropyridine carboxylate, a compound of Formula I. For example, 4-hydroxyphenylsulfonylacetone is first reacted with 2-chlorobenzaldehyde and then with methyl β-aminocrotonate to produce 4-(2-chlorophenyl)-3-(4-hydroxyphenyl)sulfonyl-5-methoxycarbonyl-2,6-dimethyl-1,4-dihydropyridine. Compounds of Formula I where $R^3$ is alkyl or alkoxyethyl can also be prepared by preparing a compound of Formula I where $R^3$ is hydrogen, and alkylating that compound with an alkyl halide or an alkoxyethyl halide in the presence of a base. For example, 4-(2-chlorophenyl)-3-(4-hydroxyphenyl)-sulfonyl-5-methoxycarbonyl-2,6-dimethyl-1,4-dihydropyridine can be alkylated with methyl iodide and potassium carbonate to form 4-(2-chlorophenyl)-3-(4-methoxyphenyl)sulfonyl-5-methoxycarbonyl-2,6-dimethyl-1,4-dihydropyridine.

The reactions in Reaction Scheme II may be carried out in the customary manner for the synthesis of dihydropyridines, e.g. as set forth in the patents referred to in the "Related Disclosures" section of this application.

Thus, the reactions described here and elsewhere in this application may be carried out in the presence or absence of diluents, condensation agents and/or catalytic agents, at lowered, normal, or elevated temperatures and, if appropriate, in a closed vessel; and one of ordinary skill in the art will be able, having regard to this disclosure and the references herein, and his own knowledge, to determine suitable reaction conditions without undue experimentation.

Compounds of Formula I*

The preparation of single isomers of optically active compounds of Formula I is shown in the following Reaction Scheme III:

REACTION SCHEME III

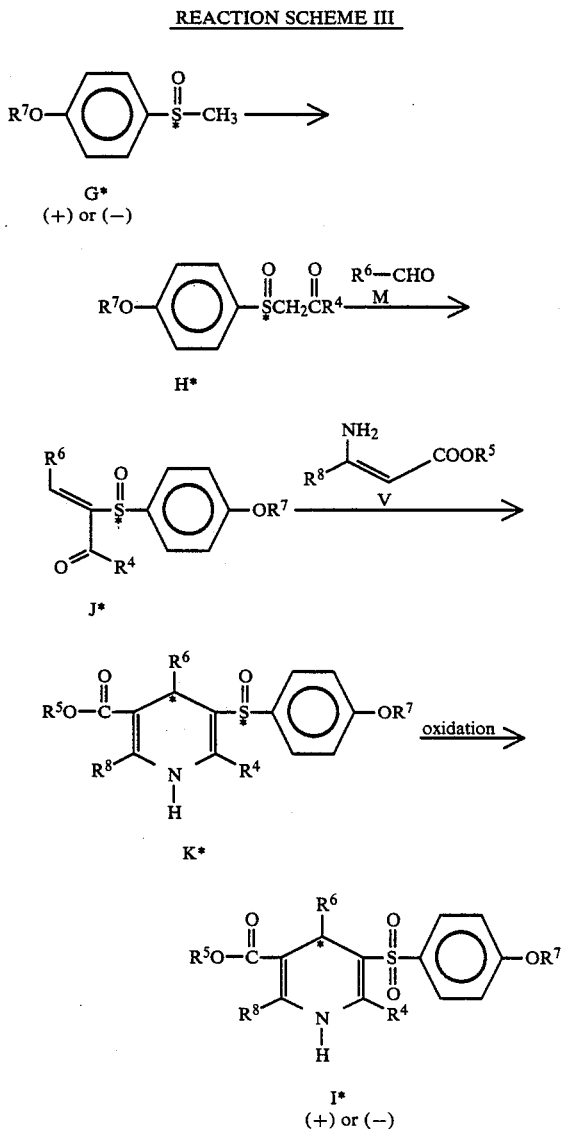

* denotes chiral compound wherein
$R^4$ and $R^8$ are hydrogen, lower alkyl, —$NR^9R^{10}$, or nitro;

$R^5$ is hydrogen, lower alkyl, lower alkoxyalkyl, or phenyl optionally substituted by one or more substituents selected from the group consisting of lower alkyl, lower alkoxy, hydroxy, halogen, lower alkoxyalkyl, nitro, and —$NR^9R^{10}$;

$R^6$ is phenyl optionally substituted by one or more substituents selected from the group consisting of lower alkyl, lower alkoxy, hydroxy, halogen, nitro, azido, trifluoromethyl, trifluoromethoxy, difluoromethoxy, —$NR^9R^{10}$, lower alkoxyalkyl, cyano, lower acyl, or lower acyloxy; or $R^6$ is

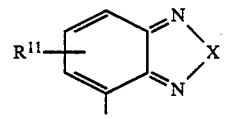

wherein X is oxygen or sulfur and $R^{11}$ is hydrogen, halogen, trifluoromethyl, nitro, hydroxy, lower alkyl, lower alkoxy, or lower alkoxyalkyl;

$R^7$ is hydrogen, lower alkyl, or lower alkoxyalkyl; and $R^9$ and $R^{10}$ are hydrogen or lower alkyl.

Compounds of Formula M and Formula V are commercially available from, i.a., Aldrich Chemical Company. Optically active sulfoxides of Formula G* may be prepared by the method of Pitchen et al., *J. Am. Chem. Soc.*, 106, 8188, (1984). Acylation of the methyl group of a compound of Formula G* by condensation of the anion with an acylating agent provides an optically active sulfinyl ketone, a compound of Formula H*. Compounds of Formula H* are then reacted with an aldehyde of Formula M to form a sulfinyl benzylidene derivative of Formula J*. Condensation with an alkyl β-aminocrotonate (a compound of Formula V) then provides a diastereomeric pair of an arylsulfinyldihydropyridine of Formula K*, which can be separated by conventional means, for example, chromatography. Oxidation of the thus-separated diastereomeric sulfinyl dihydropyridines (compounds of Formula K*) with, for example, a peroxyalkanoic acid such as m-chloroperbenzoic acid, leads to single isomers of optically active compounds of Formula I*. Because asymmetric induction by the chiral sulfoxide moiety in the sulfinylbenzylidene intermediate of Formula J* leads to formation of diastereomeric mixtures of Formula K* which are substantially non-racemic (typically, at least 90:10 ratios of one diastereomer to the other), it leads to approximately 90% or greater efficiency in production of a desired isomer of a compound of Formula I*. This process thus essentially embodies a transfer of chirality from the sulfur atom of the starting sulfoxide of Formula G* to C-4 of the dihydropyridine product of Formula I*, with the sulfur atom becoming non-chiral in the product, without the intervention of extraneous chiral reagents (such as those required to form diastereomeric salts or esters). It thus provides a route from readily prepared chiral starting materials without the use of other chiral reagents to single isomers of compounds of Formula I*, which route is extremely efficient when compared to resolution processes (since they inherently have a maximum yield of a desired isomer of only 50%).

Reaction conditions for the preparation of the sulfinyl ketones of Formula H* from the chiral aryl methyl sulfoxides of Formula G* are those conventional for the acylation of the methyl group of a methyl sulfoxide, e.g. as set forth in Houben-Weyl, "Methoden der organischen Chemie", Vol. E11, pp. 783–4 (1985) and references therein. Thus, the sulfoxide, dissolved in an aprotic solvent, is reacted with a strong base to form an anion, to which is added an acylating agent, such as an ester. Reaction conditions for the preparation of the sulfinyl dihydropyridines of Formula K* from the sulfinyl ketones of Formula H* are those conventional for such dihydropyridine synthetic reactions, as discussed before for the preparation illustrated for sulfonyl dihydropyridines in Reaction Scheme II. Reaction conditions for the oxidation of the sulfinyl dihydropyridines of Formula K* to the desired sulfonyl dihydropyridines of Formula I* are those conventional for the oxidation of sulfoxides to sulfones, e.g. as set forth in Houben-Weyl, "Methoden der organischen Chemie", Vol. E11, pp. 1194–5 and 1200–2 (1985), and references therein. Thus, an oxidizing agent such as a peroxyalkanoic acid is added to a solution of the sulfinyl dihydropyridine, and the resulting sulfonyl dihydropyridine is isolated from the reaction mixture.

The following specific description of certain embodiments of this invention is given to enable those skilled in the art to more clearly understand and practice the invention. It should not be considered as a limitation upon the scope of the invention, but merely as being illustrative and representative thereof.

PREPARATION I

A. Preparation of 4-hydroxyphenysulfonylacetone and Related Compounds of Formula C With cooling (0° C.) and overhead stirring, 1.0M NaOH (40 ml) was added to a solution of 4-hydroxythiophenol (5 g) in methanol (260 ml). The solution was then treated with chloroacetone (4.4 g), with pH dropping to 5. After 5 minutes a slurry of OXONE ® (40 g) in water (volume equal to methanol) was added rapidly. After an additional 5 minutes, the mixture was filtered and the precipitate was washed with diethyl ether. The methanol was removed in vacuo. The remaining aqueous solution was then extracted 3 times with diethyl ether.

The organic solution was then extracted 3 times with 5% NaOH, and the combined aqueous phase was acidified. The resulting precipitate was filtered, washed with $H_2O$, and dried in vacuo to yield 4-hydroxyphenylsulfonylacetone, m.p. 118°–121° C.

B. Proceeding in a similar manner, but substituting the 4-hydroxythiophenol with other corresponding thiophenols of Formula A, (which may be commercially obtained), the following compounds of Formula II are prepared:
4-methoxyphenylsulfonylacetone;
4-ethoxyphenylsulfonylacetone;
4-propoxyphenylsulfonylacetone;
4-butoxyphenylsulfonylacetone;
4-isopropoxyphenylsulfonylacetone;
4-t-butoxyphenylsulfonylacetone;
4-s-butoxyphenylsulfonylacetone;
4-methoxyethoxyphenylsulfonylacetone;
4-ethoxyethoxyphenylsulfonylacetone;
4-propoxyethoxyphenylsulfonylacetone;
4-butoxyethoxyphenylsulfonylacetone;
4-isopropoxyethoxyphenylsulfonylacetone;
4-t-butoxyethoxyphenylsulfonylacetone; and
4-s-butoxyethoxyphenylsulfonylacetone.

PREPARATION II

A. Preparation of (−)-4-methoxyphenylsulfinylacetone and Related Compounds of Formula H*

To a solution of lithium diisopropylamide prepared from diisopropylamine (27.3 g) and n-butyl lithium (161.75 ml, 1.6M) in tetrahydrofuran (700 ml), was added a solution of (−)-methyl methoxyphenyl sulfoxide (20 g) in tetrahydrofuran (40 ml) at −20° C. After 15 minutes, ethyl acetate (22.8 g) was added and the mixture was allowed to reach room temperature. After quenching with $NaH_2PO_4$, the solvent was removed in vacuo and the residue was extracted with ether. The extract was purified by chromatography on silica gel (1:1 acetone/hexane) to give (−)-4-methoxyphenylsulfinylacetone, m.p. 56°–58° C., $[\alpha]_D = -149.8°$ (C=0.032, methanol).

B. Proceeding in a similar manner, but substituting other appropriate sulfoxides for (−)-methyl methoxyphenyl sulfoxide, the following compounds are made:
(+)-4-methoxyphenylsulfinylacetone
(−)-4-hydroxyphenylsulfinylacetone;
(+)-4-hydroxyphenylsulfinylacetone;
(−)-4-ethoxyphenylsulfinylacetone;
(+)-4-ethoxyphenylsulfinylacetone;
(−)-4-propoxyphenylsulfinylacetone;
(+)-4-propoxyphenylsulfinylacetone;
(−)-4-butoxyphenylsulfinylacetone;
(+)-4-butoxyphenylsulfinylacetone;
(−)-4-isopropoxyphenylsulfinylacetone;
(+)-4-isopropoxyphenylsulfinylacetone;
(−)-4-t-butoxyphenylsulfinylacetone;
(+)-4-t-butoxyphenylsulfinylacetone;
(−)-4-s-butoxyphenylsulfinylacetone; and
(+)-4-s-butoxyphenylsulfinylacetone.

PREPARATION III

A. Preparation of (−)-4-(2-chlorophenyl)-3-(4-methoxyphenyl)sulfinyl-5-methoxy-carbonyl-2,6-dimethyl-1,4-dihydropyridine and Related Compounds of Formula K*

A solution of (−)-4-methoxyphenylsulfinylacetone (10.0 g), prepared as in Preparation II above, 2-chlorobenzaldehyde (7.3 g), and NH4OAc (100 mg) in toluene (150 ml) was heated at reflux using a Dean-Stark water separator for 2 hours. About 90 ml of the solvent was removed in vacuo. Methyl β-aminocrotonate (11.5 g) and methanol (75 ml) were added to the remaining solution. After heating at reflux for 20 hours, the reaction mixture was cooled and evaporated to dryness. The residue was chromatographed on silica gel (1:1 dichloromethane/ethyl acetate) to give the two pure sulfinyldihydropyridine diastereomers in a ratio of approximately 10:1. The major isomer was (−)-4-(2-chlorophenyl)-3-(4-methoxyphenyl)sulfinyl-5-methoxycarbonyl-2,6-dimethyl-1,4-dihydropyridine, m.p. 188°–190° C., $[\alpha]_D = -27°$ (C=0.060, methanol).

B. Proceeding in a similar manner, but replacing (−)-4-methoxyphenylsulfinylacetone with other appropriate acetones, the following compounds are prepared:
(−)-4-(2-chlorophenyl)-3-(4-ethoxyphenyl)sulfinyl-5-methoxycarbonyl-2,6-dimethyl-1,4-dihydropyridine;
(−)-4-(2-chlorophenyl)-3-(4-propoxyphenyl)sulfinyl-5-methoxycarbonyl-2,6-dimethyl-1,4-dihydropyridine;
(−)-4-(2-chlorophenyl)-3-(4-butoxyphenyl)sulfinyl-5-methoxycarbonyl-2,6-dimethyl-1,4-dihydropyridine;
(−)-4-(2-chlorophenyl)-3-(4-isopropoxyphenyl)sulfinyl-5-methoxycarbonyl-2,6-dimethyl-1,4-dihydropyridine;
(−)-4-(2-chlorophenyl)-3-(4-t-butoxyphenyl)sulfinyl-5-methoxycarbonyl-2,6-dimethyl-1,4-dihydropyridine;
(−)-4-(2-chlorophenyl)-3-(4-s-butoxyphenyl)sulfinyl-5-methoxycarbonyl-2,6-dimethyl-1,4-dihydropyridine.
(+)-4-(2-chlorophenyl)-3-(4-methoxyphenyl)sulfinyl-5-methoxycarbonyl-2,6-dimethyl-1,4-dihydropyridine;
(+)-4-(2-chlorophenyl)-3-(4-ethoxyphenyl)sulfinyl-5-methoxycarbonyl-2,6-dimethyl-1,4-dihydropyridine;
(+)-4-(2-chlorophenyl)-3-(4-propoxyphenyl)sulfinyl-5-methoxycarbonyl-2,6-dimethyl-1,4-dihydropyridine;

(+)-4-(2-chlorophenyl)-3-(4-butoxyphenyl)sulfinyl-5-methoxycarbonyl-2,6-dimethyl-1,4-dihydropyridine;
(+)-4-(2-chlorophenyl)-3-(4-isopropoxyphenyl)sulfinyl-5-methoxycarbonyl-2,6-dimethyl-1,4-dihydropyridine;
(+)-4-(2-chlorophenyl)-3-(4-t-butoxyphenyl)sulfinyl-5-methoxycarbonyl-2,6-dimethyl-1,4-dihydropyridine; and
(+)-4-(2-chlorophenyl)-3-(4-s-butoxyphenyl)sulfinyl-5-methoxycarbonyl-2,6-dimethyl-1,4-dihydropyridine.

C. Proceeding in a similar manner, but replacing 2-chlorobenzaldehyde with 2,3-dichlorobenzaldehyde, the following compounds are made:
(−)-4-(2,3-dichlorophenyl)-3-(4-methoxyphenyl)sulfinyl-5-methoxycarbonyl-2,6-dimethyl-1,4-dihydropyridine;
(−)-4-(2,3-dichlorophenyl)-3-(4-ethoxyphenyl)sulfinyl-5-methoxycarbonyl-2,6-dimethyl-1,4-dihydropyridine;
(−)-4-(2,3-dichlorophenyl)-3-(4-propoxyphenyl)sulfinyl-5-methoxycarbonyl-2,6-dimethyl-1,4-dihydropyridine;
(−)-4-(2,3-dichlorophenyl)-3-(4-butoxyphenyl)sulfinyl-5-methoxycarbonyl-2,6-dimethyl-1,4-dihydropyridine;
(−)-4-(2,3-dichlorophenyl)-3-(4-isopropoxyphenyl)sulfinyl-5-methoxycarbonyl-2,6-dimethyl-1,4-dihydropyridine;
(−)-4-(2,3-dichlorophenyl)-3-(4-t-butoxyphenyl)sulfinyl-5-methoxycarbonyl-2,6-dimethyl-1,4-dihydropyridine;
(−)-4-(2,3-dichlorophenyl)-3-(4-s-butoxyphenyl)sulfinyl-5-methoxycarbonyl-2,6-dimethyl-1,4-dihydropyridine.
(+)-4-(2,3-dichlorophenyl)-3-(4-methoxyphenyl)sulfinyl-5-methoxycarbonyl-2,6-dimethyl-1,4-dihydropyridine;
(+)-4-(2,3-dichlorophenyl)-3-(4-ethoxyphenyl)sulfinyl-5-methoxycarbonyl-2,6-dimethyl-1,4-dihydropyridine;
(+)-4-(2,3-dichlorophenyl)-3-(4-propoxyphenyl)sulfinyl-5-methoxycarbonyl-2,6-dimethyl-1,4-dihydropyridine;
(+)-4-(2,3-dichlorophenyl)-3-(4-butoxyphenyl)sulfinyl-5-methoxycarbonyl-2,6-dimethyl-1,4-dihydropyridine;
(+)-4-(2,3-dichlorophenyl)-3-(4-isopropoxyphenyl)sulfinyl-5-methoxycarbonyl-2,6-dimethyl-1,4-dihydropyridine;
(+)-4-(2,3-dichlorophenyl)-3-(4-t-butoxyphenyl)sulfinyl-5-methoxycarbonyl-2,6-dimethyl-1,4-dihydropyridine; and
(+)-4-(2,3-dichlorophenyl)-3-(4-s-butoxyphenyl)sulfinyl-5-methoxycarbonyl-2,6-dimethyl-1,4-dihydropyridine.

EXAMPLE I

A. Synthesis of 4-(2-chlorophenyl)-3-(4-hydroxyphenyl)sulfonyl-5-methoxy-carbonyl-2,6-dimethyl-1,4-dihydropyridine and Related Compounds of Formula I.

A solution of 4-hydroxyphenylsulfonylacetone (5.7 g), 2-chlorobenzaldehyde (3.7 g), and ammonium acetate (50 mg) in toluene (50 ml) was heated at reflux using a Dean-Stark water separator for 2 hours. About 20 ml of the solvent was removed on a rotary evaporator. Methyl β-aminocrotonate (3.1 g) and methanol (40 ml) were then added to the remaining toluene solution. The resulting mixture was heated under nitrogen for 18 hours. The cooled reaction mixture was evaporated to dryness, and the residue was chromatographed on silica gel (elution with 1:3 to 1:2 ethyl acetate/hexane) to yield 4-(2-chlorophenyl)-3-(4-hydroxyphenyl)sulfonyl-5-methoxycarbonyl-2,6-dimethyl-1,4-dihydropyridine, m.p. 223°–225° C.

B. Proceeding in a similar manner, but replacing methyl β-aminocrotonate with other appropriate lower alkyl β-aminocrotonates, the following compounds of Formula I are prepared:
4-(2-chlorophenyl)-3-(4-hydroxyphenyl)sulfonyl-5-ethoxycarbonyl-2,6-dimethyl-1,4-dihydropyridine;
4-(2-chlorophenyl)-3-(4-hydroxyphenyl)sulfonyl-5-propoxycarbonyl-2,6-dimethyl-1,4-dihydropyridine;
4-(2-chlorophenyl)-3-(4-hydroxyphenyl)sulfonyl-5-butoxycarbonyl-2,6-dimethyl-1,4-dihydropyridine;
4-(2-chlorophenyl)-3-(4-hydroxyphenyl)sulfonyl-5-isopropoxycarbonyl-2,6-dimethyl-1,4-dihydropyridine;
4-(2-chlorophenyl)-3-(4-hydroxyphenyl)sulfonyl-5-s-butoxycarbonyl-2,6-dimethyl-1,4-dihydropyridine; and
4-(2-chlorophenyl)-3-(4-hydroxyphenyl)sulfonyl-5-t-butoxycarbonyl-2,6-dimethyl-1,4-dihydropyridine.

C. Proceeding in a similar manner, but replacing 2-chlorobenzaldehyde with 2,3-dichlorobenzaldehyde, the following compound of Formula I are prepared:
4-(2,3-dichlorophenyl)-3-(4-hydroxyphenyl)sulfonyl-5-methoxycarbonyl-2,6-dimethyl-1,4-dihydropyridine;
4-(2,3-dichlorophenyl)-3-(4-hydroxyphenyl)sulfonyl-5-ethoxycarbonyl-2,6-dimethyl-1,4-dihydropyridine;
4-(2,3-dichlorophenyl)-3-(4-hydroxyphenyl)sulfonyl-5-propoxycarbonyl-2,6-dimethyl-1,4-dihydropyridine;
4-(2,3-dichlorophenyl)-3-(4-hydroxyphenyl)sulfonyl-5-butoxycarbonyl-2,6-dimethyl-1,4-dihydropyridine;
4-(2,3-dichlorophenyl)-3-(4-hydroxyphenyl)sulfonyl-5-isopropoxycarbonyl-2,6-dimethyl-1,4-dihydropyridine;
4-(2,3-dichlorophenyl)-3-(4-hydroxyphenyl)sulfonyl-5-t-butoxycarbonyl-2,6-dimethyl-1,4-dihydropyridine; and
4-(2,3-dichlorophenyl)-3-(4-hydroxyphenyl)sulfonyl-5-s-butoxycarbonyl-2,6-dimethyl-1,4-dihydropyridine.

EXAMPLE II

A. Synthesis of 4-(2-chlorophenyl)-3-(4-methoxyphenyl)sulfonyl-5-methoxycarbonyl-2,6-dimethyl-1,4-dihydropyridine and Related Compounds of Formula I.

A mixture of 4-(2-chlorophenyl)-3-(4-hydroxyphenyl)sulfonyl-5-methoxycarbonyl-2,6-dimethyl-1,4-dihydropyridine (4.33 g), potassium carbonate (2.76 g), methyl iodide (5.68 g), and N,N-dimethylformamide (DMF) (25 ml) was stirred at room temperature for 24 hours. The reaction mixture was diluted with water (250 ml) and extracted with ethyl acetate. The extract was dried over magnesium sulfate, filtered, and evaporated to dryness. The residue was crystallized from ether to give 4-(2-chlorophenyl)-3-(4-methoxyphenyl)sulfonyl-5-methoxycarbonyl-2,6-dimethyl-1,4-dihydropyridine, m.p. 176°–178°.

B. Proceeding in a similar manner, but replacing methyl iodide with an appropriate lower alkyl halide, the following compounds are made:
4-(2-chlorophenyl)-3-(4-ethoxyphenyl)sulfonyl-5-methoxycarbonyl-2,6-dimethyl-1,4-dihydropyridine;

4-(2-chlorophenyl)-3-(4-propoxyphenyl)sulfonyl-5-methoxycarbonyl-2,6-dimethyl-1,4-dihydropyridine;

4-(2-chlorophenyl)-3-(4-butoxyphenyl)sulfonyl-5-methoxycarbonyl-2,6-dimethyl-1,4-dihydropyridine;

4-(2-chlorophenyl)-3-(4-isopropoxyphenyl)sulfonyl-5-methoxycarbonyl-2,6-dimethyl-1,4-dihydropyridine;

4-(2-chlorophenyl)-3-(4-t-butoxyphenyl)sulfonyl-5-methoxycarbonyl-2,6-dimethyl-1,4-dihydropyridine; and 4-(2-chlorophenyl)-3-(4-s-butoxyphenyl)sulfonyl-5-methoxycarbonyl-2,6-dimethyl-1,4-dihydropyridine.

C. Proceeding in a similar manner, but replacing methyl iodide with 2-chloroethyl lower alkyl ether, the following compound of Formula I was prepared:

4-(2-chlorophenyl)-3-(4-methoxyethoxyphenyl)sulfonyl-5-methoxycarbonyl-2,6-dimethyl-1,4-dihydropyridine, m.p. 160°-161° C.

D. Proceeding in a similar manner, the following compounds are prepared:

4-(2-chlorophenyl)-3-(4-ethoxyethoxyphenyl)sulfonyl-5-methoxycarbonyl-2,6-dimethyl-1,4-dihydropyridine;

4-(2-chlorophenyl)-3-(4-propoxyethoxyphenyl)sulfonyl-5-methoxycarbonyl-2,6-dimethyl-1,4-dihydropyridine;

4-(2-chlorophenyl)-3-(4-butoxyethoxyphenyl)sulfonyl-5-methoxycarbonyl-2,6-dimethyl-1,4-dihydropyridine;

4-(2-chlorophenyl)-3-(4-isopropoxyethoxyphenyl)sulfonyl-5-methoxycarbonyl-2,6-dimethyl-1,4-dihydropyridine;

4-(2-chlorophenyl)-3-(4-t-butoxyethoxyphenyl)sulfonyl-5-methoxycarbonyl-2,6-dimethyl-1,4-dihydropyridine; and 4-(2-chlorophenyl)-3-(4-s-butoxyethoxyphenyl)sulfonyl-5-methoxycarbonyl-2,6-dimethyl-1,4-dihydropyridine.

E. Proceeding in a similar manner, but replacing 4-(2-chlorophenyl)-3-(4-hydroxyphenyl)sulfonyl-5-methoxycarbonyl-2,6-dimethyl-1,4-dihydropyridine with 4-(2,3-dichlorophenyl)-3-(4-hydroxyphenyl)sulfonyl-5-methoxycarbonyl-2,6-dimethyl-1,4-dihydropyridine, the following compounds of Formula I are prepared:

4-(2,3-dichlorophenyl)-3-(4-methoxyethoxyphenyl)sulfonyl-5-methoxycarbonyl-2,6-dimethyl-1,4-dihydropyridine;

4-(2,3-dichlorophenyl)-3-(4-ethoxyethoxyphenyl)sulfonyl-5-methoxycarbonyl-2,6-dimethyl-1,4-dihydropyridine;

4-(2,3-dichlorophenyl)-3-(4-propoxyethoxyphenyl)sulfonyl-5-methoxycarbonyl-2,6-dimethyl-1,4-dihydropyridine;

4-(2,3-dichlorophenyl)-3-(4-butoxyethoxyphenyl)sulfonyl-5-methoxycarbonyl-2,6-dimethyl-1,4-dihydropyridine;

4-(2,3-dichlorophenyl)-3-(4-isopropoxyethoxyphenyl)sulfonyl-5-methoxycarbonyl-2,6-dimethyl-1,4-dihydropyridine;

4-(2,3-dichlorophenyl)-3-(4-t-butoxyethoxyphenyl)sulfonyl-5-methoxycarbonyl-2,6-dimethyl-1,4-dihydropyridine; and 4-(2,3-dichlorophenyl)-3-(4-s-butoxyethoxyphenyl)sulfonyl-5-methoxycarbonyl-2,6-dimethyl-1,4-dihydropyridine.

EXAMPLE III

A. Synthesis of (−)-4-(2-chlorophenyl)-3-(4-methoxyphenyl)sulfonyl-5-methoxycarbonyl-2,6-dimethyl-1,4-dihydropyridine and Related Compounds of Formula I*.

To a solution of (−)-4-(2-chlorophenyl)-3-(4-methoxyphenyl)sulfinyl-5-methoxycarbonyl-2,6-dimethyl-1,4-dihydropyridine (1.4 g), prepared as in Preparation II above, in dichloromethane (300 ml), cooled to 0° C., was added m-chloroperbenzoic acid (660 mg). After stirring for 24 hours, the reaction mixture was washed with aqueous NaHCO$_3$, dried over MgSO$_4$, and evaporated to dryness. The residue was chromatographed on silica gel (1:1 dichloromethane/ethyl acetate) and recrystallized from dichloromethane/hexane to give (−)-4-(2-chlorophenyl)-3-(4-methoxyphenyl)sulfonyl-5-methoxycarbonyl-2,6-dimethyl-1,4-dihydropyridine, m.p. 200°-202° C., $[\alpha]_D = -126°$ (C=0.031, methanol) [93% enantiomeric excess (ee)].

B. Proceeding in a similar manner, but substituting (+)-4-(2-chlorophenyl)-3-(4-methoxyphenyl)sulfinyl-5-methoxycarbonyl-2,6-dimethyl-1,4-dihydropyridine for (−)-4-(2-chlorophenyl)-3-(4-methoxyphenyl)sulfinyl-5-methoxycarbonyl-2,6-dimethyl-1,4-dihydropyridine, there was prepared (+)-4-(2-chlorophenyl)-3-(4-methoxyphenyl)sulfonyl-5-methoxycarbonyl-2,6-dimethyl-1,4-dihydropyridine, m.p. 178°-180°, $[\alpha]_D = +111°$ (C=0.030, methanol) [82% ee].

C. Proceeding in a similar manner, but substituting (−)-4-(2-chlorophenyl)-3-(4-methoxyphenyl)sulfinyl-5-methoxycarbonyl-2,6-dimethyl-1,4-dihydropyridine with other appropriate 4-phenyl-3-phenylsulfinyldihydropyridines, the following compounds were made:

(−)-4-(2-chlorophenyl)-3-(4-methoxyphenyl)sulfonyl-5-ethoxycarbonyl-2,6-dimethyl-1,4-dihydropyridine;

(−)-4-(2-chlorophenyl)-3-(4-methoxyphenyl)sulfonyl-5-propoxycarbonyl-2,6-dimethyl-1,4-dihydropyridine;

(−)-4-(2-chlorophenyl)-3-(4-methoxyphenyl)sulfonyl-5-butoxycarbonyl-2,6-dimethyl-1,4-dihydropyridine;

(−)-4-(2-chlorophenyl)-3-(4-methoxyphenyl)sulfonyl-5-isopropoxycarbonyl-2,6-dimethyl-1,4-dihydropyridine;

(−)-4-(2-chlorophenyl)-3-(4-methoxyphenyl)sulfonyl-5-t-butoxycarbonyl-2,6-dimethyl-1,4-dihydropyridine;

(−)-4-(2-chlorophenyl)-3-(4-methoxyphenyl)sulfonyl-5-s-butoxycarbonyl-2,6-dimethyl-1,4-dihydropyridine;

(−)-4-(2-chlorophenyl)-3-(4-methoxyphenyl)sulfonyl-5-methoxycarbonyl-2,6-dimethyl-1,4-dihydropyridine;

(−)-4-(2-chlorophenyl)-3-(4-ethoxyphenyl)sulfonyl-5-methoxycarbonyl-2,6-dimethyl-1,4-dihydropyridine;

(−)-4-(2-chlorophenyl)-3-(4-propoxyphenyl)sulfonyl-5-methoxycarbonyl-2,6-dimethyl-1,4-dihydropyridine;

(−)-4-(2-chlorophenyl)-3-(4-butoxyphenyl)sulfonyl-5-methoxycarbonyl-2,6-dimethyl-1,4-dihydropyridine;

(−)-4-(2-chlorophenyl)-3-(4-isopropoxyphenyl)sulfonyl-5-methoxycarbonyl-2,6-dimethyl-1,4-dihydropyridine;

(−)-4-(2-chlorophenyl)-3-(4-t-butoxyphenyl)sulfonyl-5-methoxycarbonyl-2,6-dimethyl-1,4-dihydropyridine;

(−)-4-(2-chlorophenyl)-3-(4-s-butoxyphenyl)sulfonyl-5-methoxycarbonyl-2,6-dimethyl-1,4-dihydropyridine;

(−)-4-(2-chlorophenyl)-3-(4-methoxyethoxyphenyl)sulfonyl-5-methoxycarbonyl-2,6-dimethyl-1,4-dihydropyridine;

(−)-4-(2-chlorophenyl)-3-(4-ethoxyethoxyphenyl)sulfonyl-5-methoxycarbonyl-2,6-dimethyl-1,4-dihydropyridine;

(−)-4-(2-chlorophenyl)-3-(4-propoxyethoxyphenyl)sulfonyl-5-methoxycarbonyl-2,6-dimethyl-1,4-dihydropyridine;

(−)-4-(2-chlorophenyl)-3-(4-butoxyethoxyphenyl)sulfonyl-5-methoxycarbonyl-2,6-dimethyl-1,4-dihydropyridine;

(+)-4-(2-chlorophenyl)-3-(4-methoxyphenyl)sulfonyl-5-methoxycarbonyl-2,6-dimethyl-1,4-dihydropyridine;

(+)-4-(2-chlorophenyl)-3-(4-methoxyphenyl)sulfonyl-5-methoxycarbonyl-2,6-dimethyl-1,4-dihydropyridine;

(+)-4-(2-chlorophenyl)-3-(4-methoxyphenyl)sulfonyl-5-ethoxycarbonyl-2,6-dimethyl-1,4-dihydropyridine;

(+)-4-(2-chlorophenyl)-3-(4-methoxyphenyl)sulfonyl-5-propoxycarbonyl-2,6-dimethyl-1,4-dihydropyridine;

(+)-4-(2-chlorophenyl)-3-(4-methoxyphenyl)sulfonyl-5-butoxycarbonyl-2,6-dimethyl-1,4-dihydropyridine;

(+)-4-(2-chlorophenyl)-3-(4-methoxyphenyl)sulfonyl-5-isopropoxycarbonyl-2,6-dimethyl-1,4-dihydropyridine;

(+)-4-(2-chlorophenyl)-3-(4-methoxyphenyl)sulfonyl-5-t-butoxycarbonyl-2,6-dimethyl-1,4-dihydropyridine;

(+)-4-(2-chlorophenyl)-3-(4-methoxyphenyl)sulfonyl-5-s-butoxycarbonyl-2,6-dimethyl-1,4-dihydropyridine;

(+)-4-(2-chlorophenyl)-3-(4-methoxyphenyl)sulfonyl-5-methoxycarbonyl-2,6-dimethyl-1,4-dihydropyridine;

(+)-4-(2-chlorophenyl)-3-(4-ethoxyphenyl)sulfonyl-5-methoxycarbonyl-2,6-dimethyl-1,4-dihydropyridine;

(+)-4-(2-chlorophenyl)-3-(4-propoxyphenyl)sulfonyl-5-methoxycarbonyl-2,6-dimethyl-1,4-dihydropyridine;

(+)-4-(2-chlorophenyl)-3-(4-butoxyphenyl)sulfonyl-5-methoxycarbonyl-2,6-dimethyl-1,4-dihydropyridine;

(+)-4-(2-chlorophenyl)-3-(4-isopropoxyphenyl)sulfonyl-5-methoxycarbonyl-2,6-dimethyl-1,4-dihydropyridine;

(+)-4-(2-chlorophenyl)-3-(4-t-butoxyphenyl)sulfonyl-5-methoxycarbonyl-2,6-dimethyl-1,4-dihydropyridine;

(+)-4-(2-chlorophenyl)-3-(4-s-butoxyphenyl)sulfonyl-5-methoxycarbonyl-2,6-dimethyl-1,4-dihydropyridine;

(+)-4-(2-chlorophenyl)-3-(4-methoxyethoxyphenyl)sulfonyl-5-methoxycarbonyl-2,6-dimethyl-1,4-dihydropyridine;

(+)-4-(2-chlorophenyl)-3-(4-ethoxyethoxyphenyl)sulfonyl-5-methoxycarbonyl-2,6-dimethyl-1,4-dihydropyridine;

(+)-4-(2-chlorophenyl)-3-(4-propoxyethoxyphenyl)sulfonyl-5-methoxycarbonyl-2,6-dimethyl-1,4-dihydropyridine; and (+)-4-(2-chlorophenyl)-3-(4-butoxyethoxyphenyl)sulfonyl-5-methoxycarbonyl-2,6-dimethyl-1,4-dihydropyridine.

EXAMPLE IV

The following example illustrates the preparation of representative pharmaceutical formulations containing an active compound of Formula I, e.g., (−)-4-(2-chlorophenyl)-3-(4-hydroxyphenyl)sulfonyl-2,6-dimethyl-5-methoxycarbonyl-1,4-dihydropyridine.

| I.V. Formulation | |
|---|---|
| Active compound | 0.01 g |
| Propylene glycol | 20.0 g |
| Polyethylene glycol 400 | 20.0 g |
| TWEEN ® 80 1.0 g | |
| 0.9% Saline solution qs to | 100.0 mL |

The active compound is dissolved in propylene glycol, polyethylene glycol 400 and Tween 80. A sufficient quantity of 0.9% saline solution is then added with stirring to provide 100 mL of the I.V. solution which is filtered through a 0.2 micron membrane filter and packaged under sterile conditions.

| TABLET FORMULATION | parts by weight |
|---|---|
| Active compound | 5.0 |
| Magnesium stearate | 0.75 |
| Starch | 0.75 |
| Lactose | 29.0 |
| PVP (polyvinylpyrrolidone) | 0.75 |

The above ingredients are combined and granulated using methanol as the solvent. The formulation is then dried and formed into tablets (each containing 25 mg of active compound) with an appropriate tabletting machine.

EXAMPLE V

The exceptional antihypertensive activity of the compounds of the invention via oral administration is illustrated by the following assay procedure:

Adult male spontaneously hypertensive rats, weighing from 300 to 380 g, were anesthetized with ether. The left femoral artery of each rat was cannulated for the measurement of blood pressure. The rats were then placed on their backs on a table with their heads and limbs secured by restrainers which allowed immobilization of the rats with minimal blockade of blood circulation. The rats were allowed at least 30 minutes to recover from the anesthesia before the administration of test compounds and vehicle controls.

Test compounds were two compounds of the invention, (±)-4-(2-chlorophenyl)-3-(4-methoxyphenyl)sulfonyl-5-methoxycarbonyl-2,6-dimethyl-1,4-dihydropyridine and (±)-4-(2-chlorophenyl)-3-(4-hydroxyphenyl)sulfonyl-5-methoxycarbonyl-2,6-dimethyl-1,4-dihydropyridine; a compound disclosed in German OLS 2,616,995, (±)-4-(2-nitrophenyl)-3-(4-chlorophenyl)sulfonyl-5-benzyloxycarbonyl-2,6-dimethyl-1,4-dihydropyridine; and (±)-4-(2-chlorophenyl)-3-phenylsulfonyl-5-methoxycarbonyl-2,6-dimethyl-1,4-dihydropyridine. Test compounds were dissolved in dimethyl acetamide and polyethylene glycol 400 at concentrations such that 1 mg, 3 mg, 10 mg, and 30 mg of test compounds were administered per kilogram of body weight. The rats were individually orally dosed by gavage at 4 ml/kg of body weight. Blood pressure was measured with a Statham P23Db pressure transducer and continuously recorded on a Beckman R611

Dynograph. Heart rate was computed electronically from the blood pressure signals. The initial mean blood pressure of the rats before administration of the test compounds was 165 mmHg. Effects of the test compounds and the vehicle controls were monitored for two hours after the compounds were administered. Mean blood pressure was calculated as the diastolic blood pressure plus one-third of the pulse pressure. Vehicle controls were tested in a separate assay.

In the table below, all dosages are expressed as free base equivalents and the data are expressed as mean ±S.E.

TABLE 1

| Test Compound | Percent Change in Mean Blood Pressure** Dosage | | | |
|---|---|---|---|---|
| | mg/kg | 3 mg/kg | 10 mg/kg | 30 mg/kg |
| Compound A | −8 ± 3* (5)* | −34 ± 3 (4) | −40 ± 6(4) | −44 ± 2(8) |
| Compound B | −0,'6 (2) | −12 ± 3 (6) | −38 ± 3(6) | −47 ± 3(5) |
| Compound C | # | # | −1 ± 1(3) | −26 ± 7(4) |
| Compound D | # | # | −26 ± 4(4) | −27 ± 6(4) |

*Numbers in parenthesis indicate the number of rats per test compound per dosage.
**Initial mean blood pressure was 165 mmHg.
Compound not tested at this dose.
Compound A is (±)-4-(2-chlorophenyl)-3-(4-methoxy-phenyl)sulfonyl-5-methoxycarbonyl-2,6-dimethyl-1,4-dihydropyridine.
Compound B is (±)-4-(2-chlorophenyl)-3-(4-hydroxy-phenyl)sulfonyl-5-methoxycarbonyl-2,6-dimethyl-1,4-dihydropyridine.
Compound C is (±)-4-(2-nitrophenyl)-3-(4-chlorophenyl)-sulfonyl-5-benzyloxycarbonyl-2,6-dimethyl-1,4-dihydropyridine.
Compound D is (±)-4-(2-chlorophenyl)-3-phenylsulfonyl-5-methoxycarbonyl-2,6-dimethyl-1,4-dihydropyridine.

Four adult male spontaneously hypertensive rats were prepared in the manner described above for administration of vehicle controls. The effect of the vehicles and the assay conditions on blood pressure levels and heart rates is illustrated in the following TABLE 2:

TABLE 2

| | Initial | Two Hours | t-Test[a] |
|---|---|---|---|
| Blood Pressure mm/Hg | 168 ± 4(4) | 169 ± 2(4) | n.s. |
| Heart Rate b/min | 447 ± 13(4) | 462 ± 12(4) | n.s. |

[a]Paired two-tailed t-test. Non-significant when P>0.05

From TABLE 2, it is seen that the vehicle used for the test compounds does not affect the test animals, so that the results in Table I represent the activity of the test compounds themselves. From TABLE 1, a comparison between the percent change in mean blood pressure of rats administered compounds of the invention and related compounds not of this invention clearly demonstrates the markedly superior oral antihypertensive activity of the compounds of this invention.

What is claimed is:

1. A compound as a single stereoisomer, or a mixture thereof, of the formula:

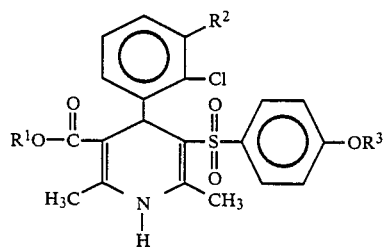

wherein $R^1$ is hydrogen or lower alkyl;
$R^2$ is hydrogen or chloro; and
$R^3$ is hydrogen, or a pharmaceutically acceptable salt thereof.

2. A compound of claim 1 in which $R^1$ is lower alkyl.

3. A compound of claim 2 in which $R^1$ is methyl.

4. The compound of claim 3 in which $R^2$ is hydrogen, namely 4-(2-chlorophenyl)-3-(4-hydroxyphenyl)sulfonyl-5-methoxycarbonyl-2,6-dimethyl-1,4-dihydropyridine.

5. The (−) isomer of the compound of claim 4, namely (−)-4-(2-chlorophenyl)-3-(4-hydroxyphenyl)-sulfonyl-5-methoxycarbonyl-2,6-dimethyl-1,4-dihydropyridine.

6. The compound of claim 3 in which $R^2$ is chloro, namely 4-(2,3-dichlorophenyl)-3-(4-hydroxyphenyl)sulfonyl-5-methoxycarbonyl-2,6-dimethyl-1,4-dihydropyridine.

7. The (−) isomer of the compound of claim 6, namely (−)-4-(2,3-dichlorophenyl)-3-(4-hydroxyphenyl)sulfonyl-5-methoxycarbonyl-2,6-dimethyl-1,4-dihydropyridine.

8. A method for treating a cardiovascular disease in a mammalian subject treatable with a calcium-entry blocker, which method comprises administration to the subject in need thereof an effective amount of a compound as a single steroisomer, or a mixture thereof, of the formula:

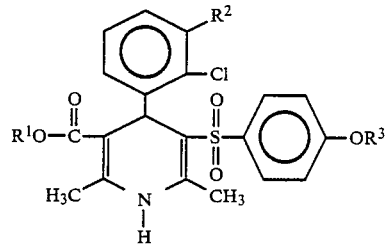

wherein $R^1$ is hydrogen or lower alkyl;
$R^2$ is hydrogen or chloro; and
$R^3$ is hydrogen, or a pharmaceutically acceptable salt thereof.

9. The method of claim 8 in which the administration is oral administration.

10. A pharmaceutical composition useful for treatment of cardiovascular disease in mammals treatable with a calcium entry-blocker, which comprises a pharmaceutically acceptable excipient and a therapeutically effective amount of a compound, as a single stereoisomer, or a mixture thereof, of the formula:

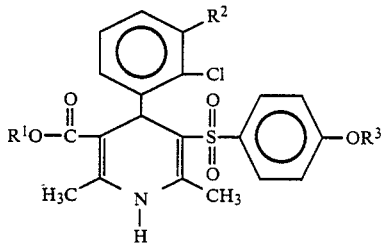

wherein $R^1$ is hydrogen or lower alkyl;
$R^2$ is hydrogen or chloro; and
$R^3$ is hydrogen,
or a pharmaceutically acceptable salt thereof.

* * * * *